United States Patent
Lovaas

Patent Number: 5,197,880
Date of Patent: Mar. 30, 1993

[54] TOOL FOR CRIMPING ENDODONTIC FILES

[76] Inventor: Leeland M. Lovaas, 40 Via Larga Vista, Bonsall, Calif. 92003

[21] Appl. No.: 444,760

[22] Filed: Dec. 1, 1989

Related U.S. Application Data

[62] Division of Ser. No. 275,213, Nov. 23, 1988, Pat. No. 4,889,487.

[51] Int. Cl.⁵ .......................... A61C 3/14; A61C 3/16; A61C 5/02; A61C 3/00
[52] U.S. Cl. ......................................... 433/159; 433/4; 433/157; 433/102
[58] Field of Search .................... 433/159, 4, 157, 158, 433/102; 140/121; 29/268; 81/424.5, 426, 426.5

[56] References Cited

U.S. PATENT DOCUMENTS

| | | | |
|---|---|---|---|
| 511,091 | 12/1893 | Neuhaus | 81/426 |
| 905,074 | 11/1908 | Hiller | 81/424.5 |
| 978,430 | 12/1910 | Braswell | 433/159 |
| 1,111,110 | 9/1914 | Trost | 433/159 |
| 1,494,775 | 5/1924 | Nelson et al. | 81/424.5 |
| 2,954,606 | 10/1960 | Peak | 433/4 |
| 3,956,950 | 5/1976 | Jamell | 81/426 |
| 4,708,651 | 11/1987 | Buchanan | 433/157 |

FOREIGN PATENT DOCUMENTS

| | | | |
|---|---|---|---|
| 667040 | 11/1938 | Fed. Rep. of Germany | 433/4 |
| 198521 | 6/1967 | U.S.S.R. | 433/4 |

*Primary Examiner*—Gene Mancene
*Assistant Examiner*—Cindy A. Cherichetti
*Attorney, Agent, or Firm*—Jerry R. Seiler

[57] ABSTRACT

A tool for crimping a substantially straight filing shaft of an endodontic file comprising a device having a first and a second jaw for being urged toward nesting engagement and for forming the bends of the shaft inserted between the jaws, the first jaw having a first crimp forming surface having a convex arch-shaped ridge and the second jaw having a concave arch-shaped cavity opposite the ridge.

9 Claims, 2 Drawing Sheets

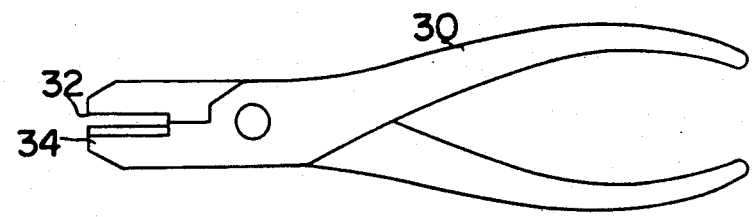
FIG. 7
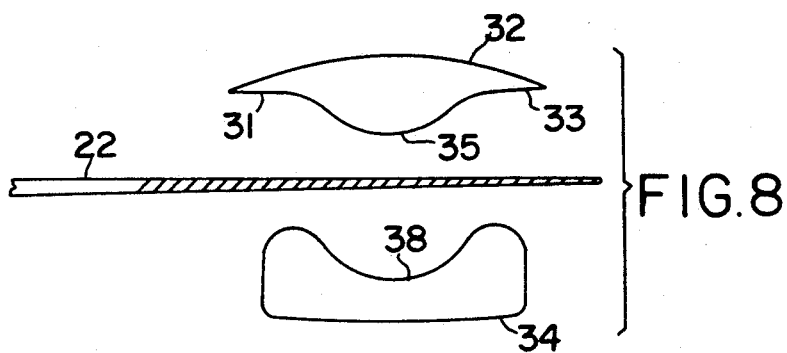
FIG. 8
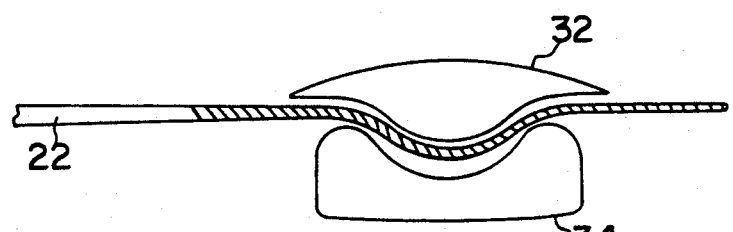
FIG. 9
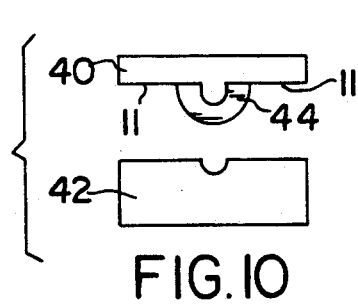
FIG. 10
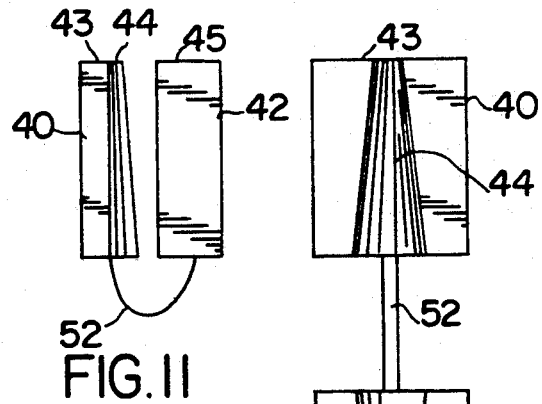
FIG. 11
FIG. 12
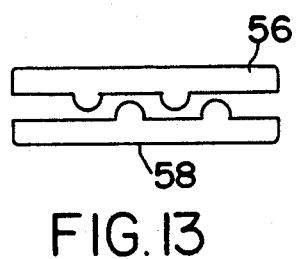
FIG. 13

TOOL FOR CRIMPING ENDODONTIC FILES

This is a division of co-pending application Ser. No. 07/275,213, U.S. Pat. No. 4,889,487, filed Nov. 23, 1988.

BACKGROUND OF THE INVENTION

Endodontic files having a tapered flexible shaft with cutting edges thereon have been used for many years for enlarging a root canal. Heretofore, these instruments have generally been of the type illustrated in FIGS. 1 and 2 incorporating a handle 10 secured at one end of the shaft 12 opposite a somewhat pointed tip. Along a portion of the length of the shaft are the cutting edges or surfaces, normally spiral, serrated, or impregnated with sharp cutting material, used for enlarging and cleaning out the canal in the root of the tooth prior to filling it with inert material. The cutting or working portions of the prior art shafts have comprised a straight portion 14 illustrated in FIG. 1 or curved portion 16 shown in FIG. 2. An example of such an instrument is illustrated in U.S. Pat. No. 4,536,159. Although these prior art devices are suitable for their it is difficult to work on and enlarge specific areas along the root canal. It is to the improvement of such an endodontic root canal enlarging device that the present invention is directed.

SUMMARY OF THE INVENTION

The present invention is directed to an improved endodontic file in which the elongated filing shaft has one or more elongated bow-shaped bends along its length. A preferred file embodiment has two or more adjacent, elongated and opposite bow-shaped bends therelong. The invention also includes the method of enlarging a root canal using such a file. In addition, a tool for crimping a filing shaft to produce a file of the invention is also included. More specific features and the advantages of such devices will be disclosed in the following detailed description.

BRIEF DESCRIPTION OF THE DRAWINGS

FIG. 7 shows a crimping tool of the invention;

FIG. 8 is a top view of the crimping jaws of the crimping tool of FIG. 7 with a straight file portion therebetween prior to being crimped;

FIG. 9 shows the crimping tool jaws forced together for crimping the filing shaft;

FIGS. 10-12 show another crimping tool embodiment, and

FIG. 13 illustrates yet another crimping tool design.

DETAILED DESCRIPTION OF THE INVENTION

Figure 1:
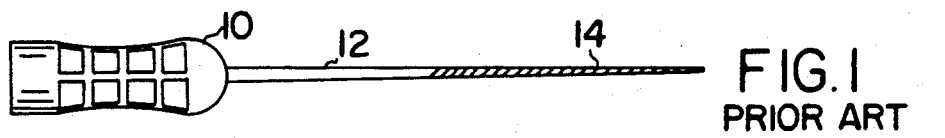
FIGS. 1 and 2 show endodontic file devices of the prior art.
Figure 2:
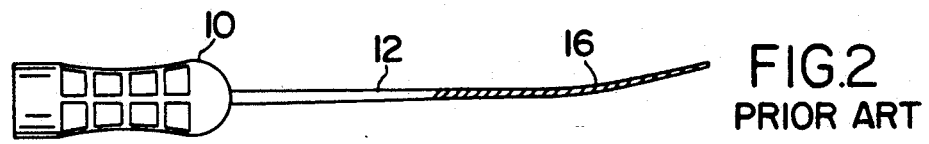
Figure 3:
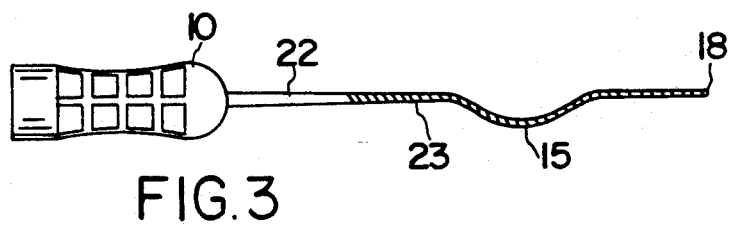
FIG. 3 shows a file of the invention having a single bow-shaped bend.

FIG. 3 illustrates a first embodiment of the invention comprising a file having a handle 10, a shaft 22 with a filing portion 23, and a single bow-shaped bend 15 located along the filing portion length. The radius (depth) of the bend as well as its length and its position along the filing shaft relative to tip 18 may be varied depending on the depth and shape of the tooth root canal to be worked on. For example, where the canal is relatively shallow, the bend may desirably be located closer to the tip as compared to a deeper canal. Similarly a greater bend radius may be preferred for enlarging a wider canal. Although each of the devices shown in FIGS. 3-5 have a handle, the invention is not so limited and includes files having no handle in which the shaft is designed to be used with the dental drill apparatus or an ultrasonic drill in which the shaft is secured in the handpiece.

Figure 6:
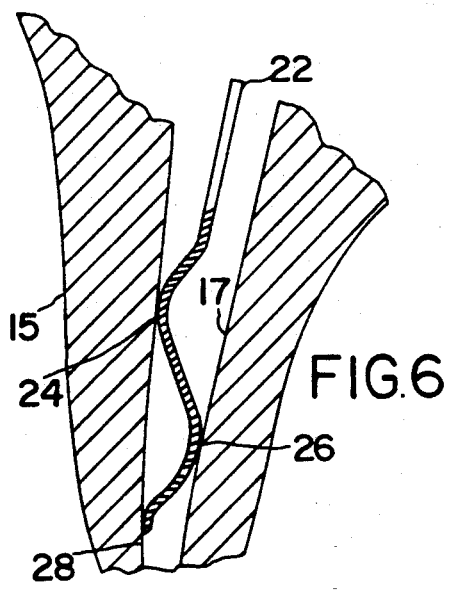
FIG. 6 shows a portion of the filing shaft of a file of the invention in a root canal illustrating the use thereof for enlargement.
Figure 5:
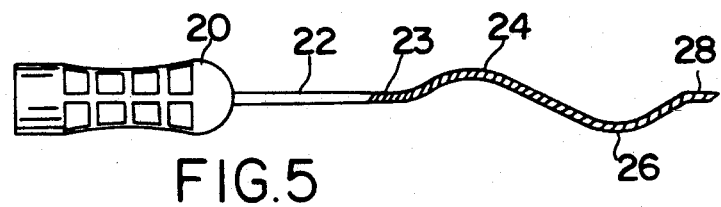
FIG. 5 illustrates a file of the invention having two bends.

A second endodontic file embodiment is illustrated in FIG. 5 comprising a handle 20 and a flexible filing shaft 22 having a serrated filing portion 23. In this embodiment, the filing portion incorporates two adjacent, elongated and opposite bow-shaped bends 24 and 26 and terminates at tip 28. Bow-shaped bends 24 and 26 are opposite, that is, they lie or extend along the same plane, but are bent or bowed outwardly in opposite directions from the axis extending along the upper portion of the filing shaft 22 and tip 28. In this device, the bends may be substantially equal in their radius or maximum distance from the elongated axis and also of substantially equal length of their arc. However, it may be preferred to have different arc lengths and/or radii of each of the respective bends for specific requirements for enlarging a root canal. For example, for many applications, it is desirable to have a smaller radius or tighter bend near the tip for working the smaller, deeper portion of a root canal and a larger radius second bend further along the shaft length from the tip. The use of such a file is shown in FIG. 6. The bends may be individually shaped as desired to meet a particular type of root canal enlargement as will be understood by those skilled in the art. Such a method and means for producing an endodontic file in which the size, shape, and number of bends may be selected by the user is a significant improvement and advantage of the present invention.

Figure 4:
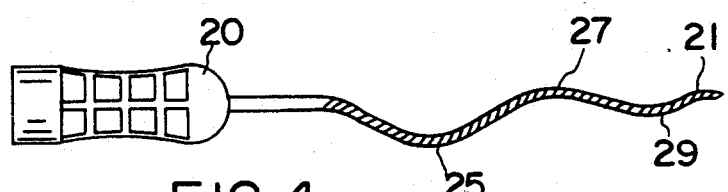
FIG. 4 illustrates a file of the invention having three contiguous bends along the filing shaft.

Another embodiment of the invention is illustrated in FIG. 4, this instrument having three adjacent elongated bow-shaped bends 25, 27 and 29. Again, preferably, the bends lie in a single plane so that bends 25 and 29 are bow-shaped in the same direction along the same plane while bend 27 is opposite and also co-planar. Where the bends lie along the same plane, by rotating the files shown in FIGS. 3-5 about 90° along the upper shaft axis, the bends would disappear to a viewer observing at the same angle. Alternatively, these bends may extend in different planes. The embodiment of FIG. 4 may also be described by bends 25 and 29 being recurves contiguous with and extending from central bow-shaped bend 27. Again, it is usually advantageous to use a smaller bend nearer tip 21 for preparing tapered root canals. In the embodiment, bend 29 is smaller than either bend 27 or 25, and bend 25 is larger than bend 27. Thus,, the bends increase in size between tip 21 and handle 20. Other devices may include additional curves or bends of the same or different sizes, which may be selectively formed to meet specific endodontic root canal enlarging needs.

In FIG. 6, a cross-section of a portion of a tooth root 15 having a canal 17 is shown with an instrument of FIG. 5 used for enlarging the canal. Shaft 22 is shown extending into the canal with first bend 24 being urged against one side of the canal and opposite bend 26 urged against the other side of the canal. The filing surface along the straight portion of the shaft adjacent tip 21 is also urged along the canal side. Thus, the endodontist may exert filing pressure at three different positions simultaneously when using such an instrument. With the filing shaft being somewhat flexible axially it will be evident that a user can move the file upwardly and downwardly reciprocally in the canal and with the bends forced against the length of the interior wall a much greater control for enlarging the canal may be achieved. The file may also be rotated so that the user is able to be selective in filing and enlarging different portions or areas of the canal wall.

FIG. 7 illustrates a device for crimping a filing shaft to form a file as previously described comprising a crimping tool 30 having first and second jaws 32 and 34. The crimping tool is similar to pliers with the opposing jaws being shaped to achieve the bow-shaped bends as previously described along the file length. In FIG. 8, first jaw 32 having a bow-shaped crimp forming surface comprises a convex arched-shaped ridge 35 with recurve surfaces 31 and 33 extending along opposite sides of the ridge. The opposite crimping surface of second jaw 34 has a concave arched-shaped cavity 38 which receives the convex ridge 35 when the jaws are urged together in the crimping operation as illustrated in FIG. 9. The file shaft is placed between the jaws so that the elongated shaft axis is substantially or generally normal to the axis of the elongated convex ridge. To form a device of the invention as shown in FIG. 3, the user simply inserts the serrated portion of an endodontic filing shaft 22 between the open jaws as illustrated in FIG. 8, holding the file with one hand, and with the other hand, holding and squeezing the crimping tool handles so that the opposite jaws are urged together.

In FIGS. 10-12 there is shown another embodiment of a crimping tool incorporating a pair of opposite crimp jaws 40 and 42. In FIG. 10, the device is viewed from the top end of the crimping jaws, FIG. 11 shows the side view thereof, and FIG. 12 is a plan view of the open jaw surfaces. A spring connector 52 is biased to keep the jaws slightly spread when not in use as shown in FIG. 11. The connector may be made of a spring metal or even a plastic unitary with the jaw components, such that the entire tool could be relatively inexpensive to mold from plastic stock. In this embodiment, the convex crimping ridge 44 has a narrowed radius at the top and is tapered along its length to a wider bottom in the shape of a segment or section of a frustum of a cone. The opposite jaw 42 has a convex cavity 46, also gradually tapered, so that ridge 44 will be received and nest therein when the jaws are closed. Recruve surfaces 11 extend along opposite sides of ridge 44. Using such a device having a tapered ridge and cavity the user can select the radius and length of the bow-shaped bends by placing the shaft higher or lower in the crimping tool to achieve the desired bend radius and length. Thus, if the file shaft is placed closer to the upper end of top jaw surfaces 43 and 45 the radius and length of the bow-shaped bend will be smaller as compared to placing the file and crimping it near the bottom of the jaws. Accordingly, such a tool may be shaped so that the user may be selective in performing the desired shapes and sizes of the bends along the file length. Moreover, using such crimping tools as illustrated also allows the user to select the location of the bends along the file length as desired. Although the radius of the ridge and cavity are shown as being gradually tapered, the taper may be stepped or segmented. In such a device, a plurality of different ridge segments, each having a different radius, may be present on one jaw, preferably stepped from narrow to larger radius, with a concave cavity similarly located on the opposite jaw. Such a device is equivalent to that shown and may allow the user to more easily select specific radius bends.

In FIG. 13 yet another crimping tool embodiment is illustrated in which multiple bends may be achieved in a single crimping action. Using the device shown, crimping a shaft between jaws 56 and 58 will result in four bends being formed simultaneously. Such a multiple crimping tool may incorporate features of the previously described tools. These as well as other embodiments and advantages within the purview of the invention will be evident to those skilled in the art.

I claim:

1. A tool for crimping a substantially straight filing shaft of an endodontic file comprising a pair of opposite crimping members a first of said members having a first crimping surface and a second of said members having a second crimping surface, said first and second crimping surfaces facing one another, and a spring connector extending between and attached to each of said crimping members and biased for holding said first and second crimping surfaces spaced apart, said first surface having a convex arch-shaped ridge tapered along its length in the shape of a section of a cone having an increasing radius between a first and second end thereof, and said second surface having a concave arch-shaped cavity tapered along its length in the concave shape of a section of a cone for receiving said ridge, said first surface having recurve forming surfaces extending on opposite sides of said ridge said first and second surfaces capable forming a bow-shaped bend along a filing shaft of an endodontic file placed therebetween when said crimping members are urged together against the bias of said spring connector.

2. A tool of claim 1 wherein said ridge extends along a first axis on said first crimping member, and said cavity extends along a second axis on said second crimping member, said first and second axis being substantially parallel, and wherein said spring connector is secured to said first crimping member along said first axis and to said second crimping member along said second axis.

3. A tool of claim 2 wherein said crimping members are formed of plastic and said spring connected is metal.

4. A tool of claim 2 wherein said crimping members and said spring connector comprise a unitary plastic device.

5. A tool for forming an arch-shaped bend along a substantially straight filling shaft of an endodontic file, said tool having first and second crimping surfaces for being urged together to form said bend on said shaft inserted therebetween, said first crimping surface having a convex arch-shaped ridge tapered along its length in the shape of a segment of a frustum of a cone having an increasing radius therealong, and recurve forming surfaces extending on opposite sides of said ridge, and said second crimping surface having a concave arch-shaped cavity opposite said ridge.

6. A tool of claim 5 wherein said concave cavity is tapered along its length opposite the taper of said convex ridge, whereby said ridge is received in said cavity when said jaws are closed.

7. A tool for forming one or more arch-shaped bends along a substantially straight filling shaft of an endodontic file, said tool having first and second jaws, said first jaw having one or more elongated axially parallel ridges thereon and said second jaw having a plurality of elongated axially parallel ridges therein, said plurality of ridges of said second jaw being parallel with and offset axially relative to said one or more ridges of said first jaw, said ridges extending along said respective jaws between opposite sides thereof, and each of said jaws having opposite recurve forming surfaces extending substantially along the length of said jaw between a ridge and a side thereof.

8. A tool of claim 7 having a spring connector extending between and attached to each of said first and second jaws and biased for holding said jaws spaced apart.

9. A method of forming an endodontic file having a plurality of bow-shaped bends comprising placing a substantially straight filing shaft of an endodontic file in a device having a first jaw comprising an elongated convex ridge having a tapered radius along its length, and a second jaw comprising an elongated concave arch-shaped cavity having a tapered radius along its length for receiving said ridge when said jaws are closed, whereby the axis of said substantially straight filing shaft is substantially normal to the axis of said ridge and said cavity, said filing shaft being positioned along said ridge at a first radius thereof, closing said jaws to form a first bend having a first radius along said filing shaft, opening said jaws, moving a straight portion of said filing shaft to a second position along the length of said ridge and substantially normal thereto, said second position corresponding to a second radius along said ridge, and closing said jaws to form a second bend having a second radius.

* * * * *